United States Patent [19]

Straith

[11] Patent Number: 4,580,560
[45] Date of Patent: Apr. 8, 1986

[54] DRAIN INSERTER

[76] Inventor: Richard E. Straith, 17100 W. 12 Mile Rd., Suite 1, Southfield, Mich. 48076

[21] Appl. No.: 580,625

[22] Filed: Feb. 16, 1984

[51] Int. Cl.⁴ .............................................. A61B 17/00
[52] U.S. Cl. ................................................ 128/303 R
[58] Field of Search ................... 128/DIG. 26, 303 R, 128/200.26; 124/18, 19

[56] References Cited

U.S. PATENT DOCUMENTS

| 1,452,902 | 4/1923 | Williamson | 124/18 |
| 2,657,691 | 11/1953 | Nordstrom | 128/303 R |
| 3,556,072 | 1/1971 | Levin | 124/19 |

Primary Examiner—Michael H. Thaler
Attorney, Agent, or Firm—Harness, Dickey & Pierce

[57] ABSTRACT

An elongate, easily flexible and readily deformable drain inserter for use in the placement of tubular suction catheters in patients following surgery.

4 Claims, 7 Drawing Figures

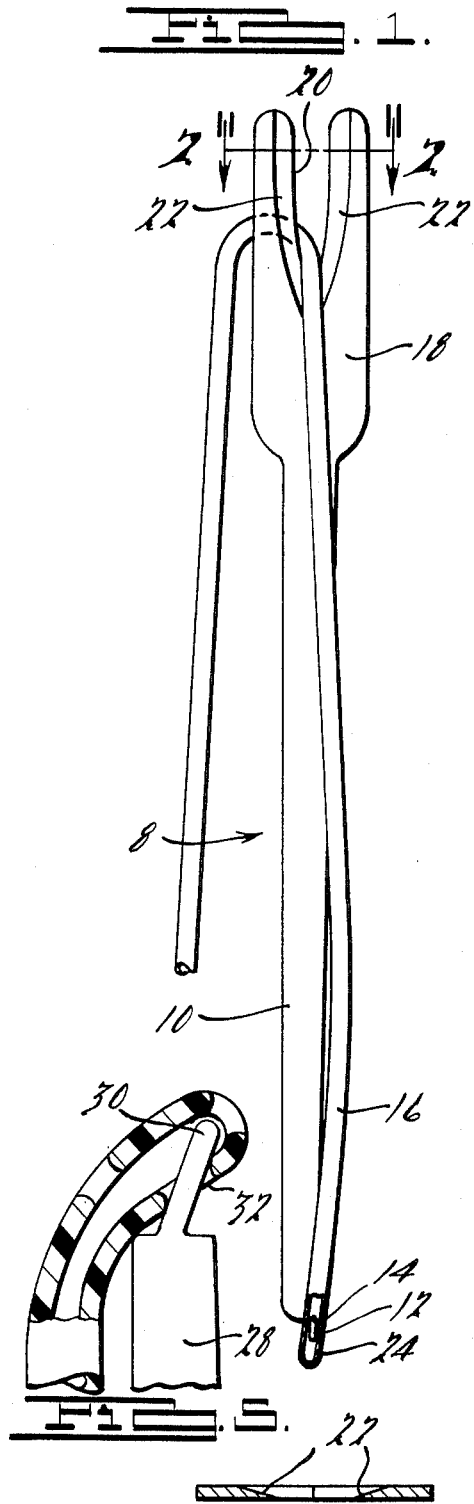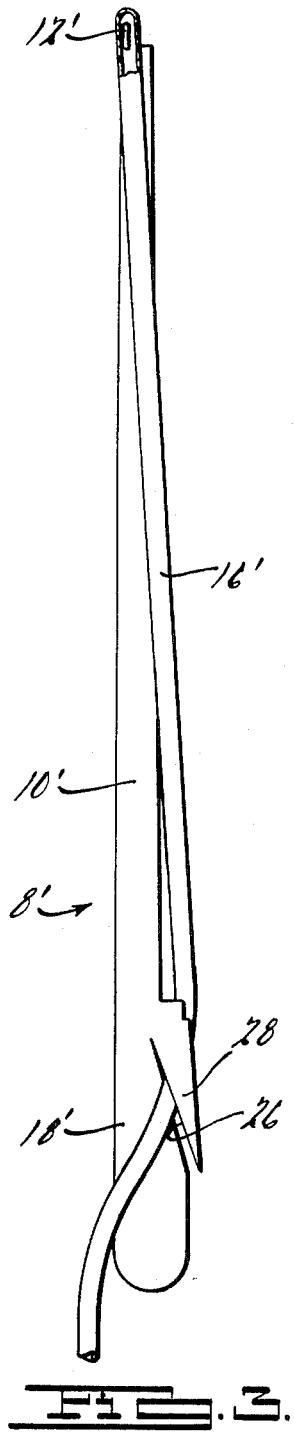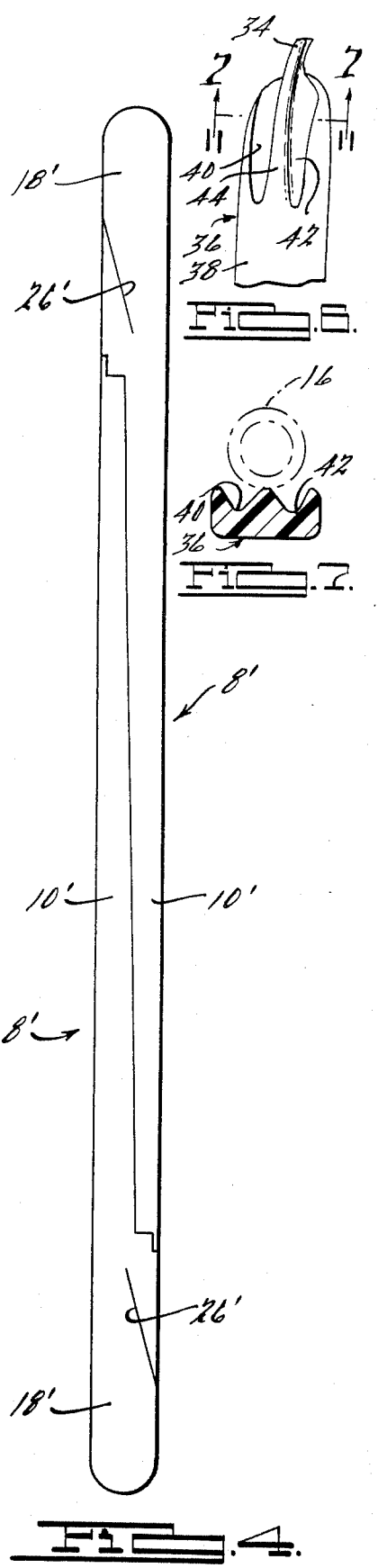

DRAIN INSERTER

BACKGROUND OF THE INVENTION

It is customary after surgery to place the perforate inner drainage end of a suction catheter inserted through the incision at a location inside the body of the patient where fluids tend to accumulate so that the fluids are drained by a light suction pump attached to the outer end of the catheter. These catheters are a conventional type usually extrusion molded of a plastic resin material. They are resilient, are of relatively small diameter, and are easily flexed. As a consequence, it sometimes is difficult to place the perforate inner end of the catheter drain precisely in the desired location. The usual practice is for the surgeon to clamp the end of the catheter with a hemostat, insert both through the incision to the desired place in the patient, then release the clamp and removes the hemostat leaving the drain in place. What happens all to often, however, is that there is insufficient room to fully disengage the hemostat from the catheter so that, when the hemostat is removed, the catheter comes out with the hemostat. This may happen repeatedly wasting valuable operating time. Since the surgeon usually cannot see the place where he intends to position the end of the catheter, he must rely on his sense of feel to place it precisely in the right location and this frequently is difficult to do because of the inherent physical characteristics of the catheter. The catheter also sometimes folds back upon itself and the perforated inner end does not always move in the direction in which the catheter is pushed so that, as a practical matter, it sometimes is not properly placed and as a result, the catheter does not do the job that it is intended to do.

The purpose of the present invention is to provide a device that can be detachable fastended to the catheter and that, when so attached, will support the latter for substantially the entire inserted length thereof and that is easily flexible and, in at least one form of the invention, readily deformable so that it can be formed in situ in accordance with the exigencies of the particular situation to permit the surgeon to place the perforated end of the catheter precisely in a desired location within the incision even though the location is remote from the incision or difficultly accessible.

SUMMARY OF THE INVENTION

Succinctly, the instrument of this invention comprises an elongate, essentially narrow body that can be easily flexed and, as suggested, in some instances, readily deformed to a desired configuration but that is sufficiently stiff to hold at least for a short time the configuration in which it is formed. A longitudinal extension at the forward end of the body is inserted through one of the perforations at the drainage end of the catheter so that, when inserted into the catheter opening, the extension is releasably attached to the drainage end as long it remains in the opening. The extension should fit relatively loosely in the standard or conventional size perforation in the catheter so that the extension can be readily withdrawn from the perforation and the inserter easily detached from the catheter. In practice, the catheter is stretched from the extension rearwardly along the body of the instrument in such a way that it tends to assume the shape or configuration of the instrument, and it is detachably fastened to a suitable clamping means provided at or adjacent to a handle at the outer end of the instrument. Thus, the surgeon can easily bend or deform the instrument to whatever shape is required to permit precise placement of the catheter within the incision and, if the inserter is deformable as well as flexible, the instrument will retain this shape at least long enough to permit accurate placement of the drainage end of the catheter. The portion of the catheter engaged by the clamp outside the incision is then released so that the resiliency of the catheter tends to "shoot" the impaled opening forwardly off the extension to disengage the drainage end from the body and at the same time leave the catheter which is completely disengaged from the body of the instrument precisely placed within the incision. The instrument can then be retracted without disturbing the catheter and removed from the incision. Then, when the catheter is taped to the body of the patient adjacent to the incision in the conventional manner, the catheter remains in the inserted position.

DESCRIPTION OF THE DRAWINGS

FIG. 1 is a plan view showing a conventional catheter of the type involved here detachably fastened to a drain inserter instrument embodying the invention;

FIG. 2 is an enlarged, transverse sectional view taken on the line 2—2 of FIG. 1;

FIG. 3 is a plan view similar to FIG. 1 but showing a modified form of drain inserter embodying the invention;

FIG. 4 is a plan view illustrating the manner in which the drain inserter shown in FIG. 3 can be made easily and economically from a single strip of a suitable material of uniform width by a conventional stamping and forming operation;

FIG. 5 is a view showing the terminal portion of another modified form of drain inserter and illustrating the same in association with the terminal portion of a conventional drainage tube or catheter, the inserter being shown in side elevation and the drainage tube being shown partly in elevation and partly in section for clearness of illustration;

FIG. 6 is a view showing the terminal portion of still another modified form of drain inserter embodying the invention; and FIG. 7 is a transverse sectional view taken on the line 7—7 of FIG. 6 showing the inserter in full lines and a catheter tube in broken lines associated with the inserter as it is in use.

DESCRIPTION OF THE PREFERRED EMBODIMENT

Reference is first had to FIG. 1 which shows one form of the drain inserter 8 embodying the invention. More particularly the drain inserter 8 there shown comprises an elongate body of sufficiently narrow width to permit easy insertion thereof through any, or substantially any, incision normally made during a surgical operation and of sufficient length to reach any location in which a drain inserter normally must be placed following surgery. The body 10 can be made of any suitable, easily flexible, and readily deformable material and that, at the same time, is sufficiently stiff to retain at least temporarily the configuration to which it is formed. It can be made of any material having these characteristics that can be sterilized such as a suitable metal or the like.

At its forward end, the body 10 is formed, preferably adjacent one edge thereof, with a longitudinal extension 12 that is sufficiently narrow to be easily insertable through and removed from a perforation 14 with which conventional suction catheters 16 are provided at or adjacent to the drainage end 24 thereof, as shown in FIG. 1. At the opposite end thereof, the body 10 is provided with a handle 18 of a suitable size and shape that permits the body to be easily held and manually manipulated as required to insert the forward or inner end thereof, with the catheter attached, through a surgical incision. In the particular form of the invention here shown by way of illustration, the handle 18 is formed in one piece with the body 10; but it will be readily apparent that the handle can be formed separately and attached to the body in any suitable or conventional manner.

It is contemplated that the body 10 be provided at or adjacent to the handle 18 with a suitable means for releasably holding the catheter 16 after the drainage end 24 thereof has been impaled on the extension 12 in the manner hereinabove described and stretched back along the length of the body to the handle 18, as shown in FIG. 1. Any suitable means can be used for this purpose; but it has been found that a slit or V-shaped notch such as the notch here shown at 20 is suitable for this purpose. In the particular arrangement here shown, the notch 20 is disposed medianly of the handle 18 and it extends longitudinally inwardly from the free or outer end thereof. Also, if the body 10 is formed from an essentially thin metal strip, it may be desirable to bevel the opposed sides of the notch 20, as at 22, to define essentially thin edges capable of gripping the catheter and of holding it securely but releasably without damage thereto when the catheter is wedged into the narrow inner end of the notch.

In use, the drainage end 24 of the catheter 16 is first impaled on the extension 12, as indicated above, stretched back along the length of the body 10, and wedged in the V-notch 20. Then, when the body 10 is bent or deformed to a desired shape that permits placement of the perforated drainage end 24 at a desired location inside the incision, the catheter 16 will conform generally to the configuration of the body and will move with the latter when the surgeon manipulates the instrument to place the forward or inner end thereof and the impaled drainage end of the catheter in the desired location within the incision. Of course, if proper placement of the catheter requires that the instrument be bent laterally to one side, the body 10 preferably is bent with the catheter at the outside of the curve so that the catheter does not chord across the arc and prevent or at least interfere with movement and manipulation of the body when the latter is inserted through the incision. Of course, it may not be necessary to bend or deform the body 10 at all in some situations; but, if some deformation is necessary or desirable, a simple lateral bend is usually all that is required for proper placement of the catheter. After the body 10 has been manipulated to place the perforate end of the catheter 16 at the desired location within the incision, the catheter is pulled free of the V-notch 20. During this step, the catheter is stretched against the entire length of the body forwardly of the notch 20 so that insertion and manipulation of the instrument does not disturb or dislocate either the forward end of the body or the attached perforate end of the catheter. Then, the catheter is disengaged from the holding notch 20 and released permitting the resiliency of the material from which the catheter is formed to shoot the drainage end thereof forwardly off of the retaining extension 12 and disengaging the catheter from the body 10. The latter is then retracted slowly and carefully until it is withdrawn from the incision. In practice, this can be done easily without disturbing the perforate end 24 of the catheter 16. Manifestly, the resilient shooting action of the catheter 16 not only releases the catheter automatically from the body 10 but is also assures proper placement of the drainage end 24 of the catheter within the incision and in the location intended by the surgeon and it also assures complete disengagement of the catheter 16 from the body 10 so that the catheter is not pulled out by the instrument when it is withdrawn through the incision.

The form of the instrument illustrated by FIG. 3 is simiar to the one shown in FIG. 1 so that corresponding parts of the two devices are identified by the same numeral except that the numerals on the FIG. 3 modification are primed. More particularly, the handle 18' formed on the FIG. 3 embodiment is similar to the handle 18 with which the FIG. 1 embodiment is provided except that it projects longitudinally from one side of the body 10' and it is formed at the outer side thereof with a longitudinally and laterally inwardly extending slit 26 in place of the notch 20. It is contemplated that the slit 26 extend from one side edge of the handle 18', as shown in the drawing; and it preferably is located substantially midway of the length of the handle so that the flap 28 defined by the slit can be easily bent laterally from the plane of the body 10' without disturbing or interfering with the user's grip on the handle 18'.

In practice, the catheter 16' is impaled on a longitudinal extension 12' formed at the forward or inner end of the body 10' identically to the extension described in connection with the first form of the invention shown in FIG. 1; and, in use, the catheter is stretched in the direction of the handle and wedged into the slit 26 so that the flap 28 holds it securely but releasably under tension while the body 10' is being deformed as and if required and inserted into the incision for proper placement of the drainage end of the catheter in the manner previously described. Then, when the catheter 16 is pulled free of the slit 26 and released, the action of the catheter as it disengages itself from the instrument is the same as that described in connection with the first form of the invention.

FIG. 4 illustrates a further advantage inherent in the particular form of the body 10' shown in FIG. 3 since this particular form permits identical bodies to be formed in pairs from a metal strip of uniform width. As clearly shown in the drawing, the two instruments in each pair complement each other so that they can be made easily and inexpensively two at a time from a thin metal strip of proper width by a conventional stamping and forming operation.

The form of the invention shown in FIG. 5 is made of metal or other readily deformable material as in the forms of the invention hereinabove described. While the terminal portion only of the modification involved here is shown in the drawing, it will be understood that it has an elongate body 28 as in the first forms of the invention and that the body has a handle portion of the type shown at 18 or 18' remote from the terminal end. Further, it is contemplated that the handle of the body 28 have suitable means for releasably holding the drain or catheter as in the forms of the invention first described.

In the FIG. 5 modification the tip of the drain inserter 28 is formed at substantially the middle thereof with a suitable lontigudinal prong 30 of sufficiently small cross sectional dimension to fit readily into one of the side openings with which drainage tubes or catheters, such as the one here shown at 32, are conventionally provided. The prong 30 is bent laterally at an angle from the longitudinal axis of the inserter body so that, when a drainage tube 32 is impaled on the prong and pulled back alongside the body at the side thereof opposite the direction in which the prong is bent, the latter is better able to resist the longitudinal pull of the tube. In order to have utility the inserter must be relatively inexpensive and this fact almost dictates that the prong and body portions be made in one piece. Moreover, in order for the inserter to serve the purpose for which it is intended, it preferably is readily deformable and therefore easily bendable. The prong 30 therefore also is easily bendable and since it necessarily has to be easily insertable into and removable from an opening of the drainage tube which opening itself is of relatively small diameter, there is a problem in making the prong strong enough to withstand the pull of the drainage tube when the latter is pulled back along the inserter and secured at the handle end thereof. It has been found in this connection that the strength of the prong 30 and its resistance to the pull of the drainage tube is unexpectedly enhanced by locating it at the middle and spaced from the opposite sides of the inserter body and by bending it angularly away from the directions of pull at an appropriate of, for example, approximately 20°. In practice, of course, the prong 30 may be bent at any angle that best serves the purpose of the bent configuration and the particular angle in turn may depend to some extent on the physical characteristics of the drainage tube with which the inserter is adapted to be used as well as the contemplated conditions of use. However, an angle of approxiamtely 20° has been found satisfactory for most purposes.

Reference is now had to FIGS. 6 and 7 which show still another modified form of the invention that is primarily adapted and preeminently suited for use if the inserter is made of a plastic material. This material is particularly desirable since it permits the inserter to be injection molded easily and inexpensively in a conventional manner. In this type of inserter, any plastic material may be used that is non-toxic and that has the necessary physical properties. For example, it desirably should be able to withstand autoclave temperatures for a length of time sufficient to permit sterilization and ideally it should be essentially flexible. In this latter connection, the inserter need not be deformable as well as flexible although this is desirable.

In any event, when a plastic material is used, the inserter preferably is made in substantially the same form or shape as the modified form shown in FIG. 5. In this instance, however, the prong 34 on which the catheter is impaled is formed as an integral part of the inserter body 36, and it preferably extends longitudinally from the forward end of the body flush with the top surface 38 thereof.

In use, the prong 34 is inserted into a lateral perforation near the end of the catheter, as shown in FIG. 5, and the catheter is stretched back along the top surface 38 of the body 36 to a retaining notch, such as the one shown in FIGS. 1 or 3, provided at the rearward end of the body. The prong 34, of course, must be of sufficiently small cross sectional size to be easily insertable into and removable from the catheter perforation but, at the same time, it must be sufficiently strong to withstand the longitudinal pull of and the tension exerted by the catheter when it is stretched back along the inserter. In this connection, it has been found that the strength of the prong 34 is maximized if it is curved longitudinally and laterally away from the top surface 38. Furthermore, this particular prong configuration facilitates withdrawal of the prong from the catheter perforation and permits the inserter to be readily disengaged from the catheter after the latter has been properly placed in use. Also, the prong configuration permits the impaled end of the catheter to be shot or impelled forwardly off the inserter when the catheter is disengaged from the retaining notch at the rearward end of the inserter and manually released particularly in the case of relatively small diameter catheters that are considerably more resilient than the larger diameter ones.

If the catheter is not sufficiently resilient to be snapped off the end of the inserter, the latter must be disengaged by retracting it, and when this is done it is of course desirable that the inserter not drag the impaled end of the catheter back with it. To help insure proper placement of the catheter, the top surface 38 of the inserter body 36 is formed at opposite sides of the prong 34 with a pair of shallow longitudinal grooves 40 and 42. These grooves preferably extend through the forward end of the inserter and they are sufficiently long to define an essentially elongate narrow rib or ridge 44 therebetween against which the catheter tubing lays immediately behind the perforation in which the prong 34 is inserted. The narrow ridged top of the rib 44 reduces the area of contact between the catheter and the inserter immediately behind the prong 34 almost to a line and thus minimizes the drag or frictional resistance of the body 36 to withdrawal of the prong and minimizes also any tendency of the withdrawal motion to disturb the properly located and positioned end of the catheter inside the incision.

Having thus described the invention, I claim:

1. A drain inserter for use in surgical operations for placement of a conventional tubular suction catheter of the type having perforations at or adjacent to one end thereof in a patient, said drain inserter comprising an elongate, relatively thin, body having a handle at one end and a longitudinal extension at the other or distal end thereof, said longitudinal extension being of sufficiently small cross sectional dimension to permit easy insertion thereof into one of said perforations whereby to attach the perforated end portion of said catheter releasably to said other end of said body, and retaining means adjacent to said handle adapted to receive and hold said catheter when the latter is stretched tautly between the said extension and said retaining means, said body being of a material that is easily flexible to permit insertion of the portion thereof remote from said handle through an incision and placement of the perforated end of said catheter at a desired location in the body of the patient, said retaining means being readily releasable thereafter from said catheter to permit withdrawal of said body through said incision independently of said catheter and consequential retraction of said extension from the perforation engaged thereby without disturbing the position and orientation of the catheter and particularly the perforated end thereof in said patient, said body being substantially half as wide as said handle at the juncture thereof with said handle, said body extending longitudinally from one half-portion only of said handle, said handle defining a transverse shoulder at the juncture thereof with said body, said shoulder being stepped back at the side edge of said handle laterally remote from said body, and said step being of the same size and shape as said longitudinal extension.

2. A drain inserter as defined by claim 1 wherein said body is tapered uniformly from said handle toward said longitudinal extension.

3. A drain inserter as defined by claim 2 wherein said body and said handle are of essentially thin sheet metal.

4. A drain inserter for use in surgical operations for placement of a conventional tubular suction catheter of the type having perforations at or adjacent to one end thereof in a patient, said drain inserter comprising an elongate, relatively thin, body having a handle at one end and a longitudinal extension at the other or distal end thereof, said longitudinal extension being of sufficiently small cross sectional dimension to permit easy insertion thereof into one of said perforations whereby to attach the perforated end portion of said catheter releasably to said other end of said body, and retaining means adjacent to said handle adapted to receive and hold said catheter when the latter is stretched tautly between the said extension and said retaining means, said body being of a material that is easily flexible to permit insertion of the portion thereof remote from said handle through an incision and placement of the perforated end of said catheter at a desired location in the body of the patient, said retaining means being readily releasable thereafter from said catheter to permit withdrawal of said body through said incision independently of said catheter and consequential retraction of said extension from the perforation engaged thereby without disturbing the position and orientation of the catheter and particularly the perforated end thereof in said patient, said longitudinal extension being disposed substantially medianly of said body and substantially flush with the top surface thereof, said body being provided in the top surface thereof with grooves extending longitudinally rearwardly from the forward end of the body and at opposite sides of said longitudinal extension, and said grooves defining a narrow ridge directly behind said extension for supporting the portion of the catheter adjacent to the perforation in which the extension is inserted, whereby to minimize the drag of said body against said catheter when said inserter is retracted to withdraw the extension from said perforation and to minimize any tendency of the retracting motion to disturb the positioned end of the catheter.

* * * * *